United States Patent [19]
Njoroge et al.

[11] Patent Number: 6,071,907
[45] Date of Patent: *Jun. 6, 2000

[54] TRICYCLIC COMPOUNDS USEFUL AS FPT INHIBITORS

[75] Inventors: F. George Njoroge, Union; Yi-Tsung Liu, Morris Township; Arthur G. Taveras, Rockaway, all of N.J.

[73] Assignee: Schering Corporation, Kenilworth, N.J.

[ * ] Notice: This patent is subject to a terminal disclaimer.

[21] Appl. No.: 08/927,726

[22] Filed: Sep. 11, 1997

Related U.S. Application Data

[60] Provisional application No. 60/026,078, Sep. 13, 1996.
[51] Int. Cl.$^7$ ............... A61K 31/54; A61K 31/445; C07D 401/14; C07D 417/14
[52] U.S. Cl. ............... 514/228.2; 514/254; 514/290; 544/60; 546/93
[58] Field of Search ............... 514/228.2, 254, 514/290; 546/93; 544/60, 361

[56] References Cited

U.S. PATENT DOCUMENTS

| | | | |
|---|---|---|---|
| 4,355,036 | 10/1982 | Villani | 424/267 |
| 4,454,143 | 6/1984 | Villani | 424/263 |
| 4,826,853 | 5/1989 | Piwinski et al. | 514/290 |
| 5,089,496 | 2/1992 | Piwinski et al. | 514/253 |
| 5,151,423 | 9/1992 | Piwinski et al. | 514/254 |
| 5,393,890 | 2/1995 | Syoji et al. | 546/80 |
| 5,661,152 | 8/1997 | Bishop et al. | 514/254 |
| 5,672,611 | 9/1997 | Doll et al. | 514/325 |
| 5,684,013 | 11/1997 | Afonso et al. | 514/290 |
| 5,696,121 | 12/1997 | Bishop et al. | 514/254 |
| 5,700,806 | 12/1997 | Doll et al. | 514/290 |
| 5,703,090 | 12/1997 | Afonso et al. | 514/299 |
| 5,712,280 | 1/1998 | Doll et al. | 514/253 |
| 5,714,609 | 2/1998 | Doll et al. | 546/93 |
| 5,719,148 | 2/1998 | Bishop et al. | 514/228 |
| 5,721,236 | 2/1998 | Bishop et al. | 514/255 |
| 5,728,703 | 3/1998 | Bishop et al. | 514/254 |
| 5,874,442 | 2/1999 | Doll | 514/290 |

FOREIGN PATENT DOCUMENTS

| | | |
|---|---|---|
| 0 270 818 A1 | 6/1988 | European Pat. Off. . |
| 0 396 083 A1 | 11/1990 | European Pat. Off. . |
| 0 495 484 A1 | 7/1992 | European Pat. Off. . |
| WO 96/31477 | 10/1966 | WIPO . |
| WO 95/00497 | 1/1995 | WIPO . |
| WO 95 10516 | 4/1995 | WIPO . |
| WO 95/10514 | 4/1995 | WIPO . |
| WO 95/10515 | 4/1995 | WIPO . |
| WO 95/15949 | 6/1995 | WIPO . |
| WO 96/30018 | 10/1996 | WIPO . |
| WO 96 30362 | 12/1996 | WIPO . |
| WO 96 30363 | 12/1996 | WIPO . |
| WO 96 31478 | 12/1996 | WIPO . |
| WO97 23478 | 4/1997 | WIPO . |

OTHER PUBLICATIONS

Bishop, W. Robert, et al., Novel Tricycle Inhibitors of Farnesyl Protein Transferase, The Journal of Biochemical Chemistry, vol. 270, No. 15, pp. 30611–30618 (1995).

Kohl, Nancy E., et al., Selective Inhibition of Ras–Dependent Transformation By A Farnesyltransferase Inhibitor, Science, vol. 260, pp. 1834–1837.

Njoroge, F. George, et al., Novel Tricycle Aminoacetyl and sulfonamide inhibitors of Ras Farneysl Protein Transferase, Bioorganic & Medicinal Chemistry Letters, vol. 6, No. 24, pp. 2977–2982 (1996).

Wong, J.K., et al., Bioorganic & Medicinal Chemistry Letters, vol. 3, No. 6, pp. 1073–1078 (1993).

*Primary Examiner*—Evelyn Mei Huang
*Attorney, Agent, or Firm*—Joseph T. Majka; Henry C. Jeanette

[57] ABSTRACT

Novel tricyclic compounds and pharmaceutical compositions are disclosed which are inhibitors of the enzyme, farnesyl protein transferase. Also disclosed is a method of inhibiting Ras function and therefore inhibiting the abnormal growth of cells. The method comprises administering the novel tricyclic compound to a biological system. In particular, the method inhibits the abnormal growth of cells in a mammals such as a human.

12 Claims, No Drawings

TRICYCLIC COMPOUNDS USEFUL AS FPT INHIBITORS

The present application claims the benefit under Title 35, United States Code, 119(e) of U.S. provisional application Ser. No. 60/026,078 filed Sep. 13, 1996.

BACKGROUND

Patent application WO 95/00497 published Jan. 5, 1995 under the Patent Cooperation Treaty (PCT) describes compounds which inhibit the enzyme, farnesyl-protein transferase (FPT or FTase) and the farnesylation of the oncogene protein Ras. Oncogenes frequently encode protein components of signal transduction pathways which lead to stimulation of cell growth and mitogenesis. Oncogene expression in cultured cells leads to cellular transformation, characterized by the ability of cells to grow in soft agar and the growth of cells as dense foci lacking the contact inhibition exhibited by non-transformed cells. Mutation and/or overexpression of certain oncogenes is frequently associated with human cancer.

To acquire transforming potential, the precursor of the Ras oncoprotein must undergo farnesylation of the cysteine residue located in a carboxyl-terminal tetrapeptide. Inhibitors of the enzyme that catalyzes this modification, farnesyl protein transferase, have therefore been suggested as anticancer agents for tumors in which Ras contributes to transformation. Mutated, oncogenic forms of Ras are frequently found in many human cancers, most notably in more than 50% of colon and pancreatic carcinomas (Kohl et al., Science, Vol. 260, 1834 to 1837, 1993).

In view of the current interest in inhibitors of farnesyl protein transferase, a welcome contribution to the art would be additional compounds useful for the inhibition of farnesyl protein transferase. Such a contribution is provided by this invention.

SUMMARY OF THE INVENTION

Inhibition of farnesyl protein transferase by tricyclic compounds of this invention has not been reported previously. Thus, this invention provides a method for inhibiting farnesyl protein transferase using tricyclic compounds of this invention which: (i) potently inhibit farnesyl protein transferase, but not geranylgeranyl protein transferase I, in vitro; (ii) block the phenotypic change induced by a form of transforming Ras which is a farnesyl acceptor but not by a form of transforming Ras engineered to be a geranylgeranyl acceptor; (iii) block intracellular processing of Ras which is growth in culture induced by transforming Ras. Several compounds of this invention have been demonstrated to have anti-tumor activity in animal models.

This invention provides a method for inhibiting the abnormal growth of cells, including transformed cells, by administering an effective amount of a compound of this invention. Abnormal growth of cells refers to cell growth independent of normal regulatory mechanisms (e.g., loss of contact inhibition). This includes the abnormal growth of: (1) tumor cells (tumors) expressing an activated Ras oncogene; (2) tumor cells in which the Ras protein is activated as a result of oncogenic mutation in another gene; and (3) benign and malignant cells of other proliferative diseases in which aberrant Ras activation occurs.

Tricyclic compounds of the present invention include the following:

4-[8-Chloro-3,7-dibromo-5,6-dihydro-11H-benzo[5,6] cyclohepta[1,2-b]pyridin-11-yl]-1-(4-thiomorpholinylacetyl)piperidine 4-[8-Chloro-3,7-dibromo-6,11-dihydro-5H-benzo[5,6] cyclohepta[1,2-b]pyridin-11-yl]-1-(4-thiomorpholinylacetyl)piperidine S-oxide;

(+,−)-1-(3-bromo-8,10-dichloro-5-ethyl-6,11-dihydro-5H-benzo[5,6]cyclohepta[1,2-b]pyridin-11-yl)-4-(4-pyridinylacetyl)piperazine N4-oxide (+)-4-(3-bromo-8,10-dichloro-6,11-dihydro-5H-benzo[5,6] cyclohepta[1,2-b]pyridin-11-yl)-1-[2-(1,3-dihydro-1,3-dioxo-2H-isoindol-2-yl)-1-oxoethyl]piperidine; and (+)-4-(3,10-Dibromo-8-chloro-6,11-dihydro-5H-benzo[5,6] cyclohepta[1,2-b]pyridin-11(R)-yl)-1-[(1-oxopropyl-4-piperidinyl)acetyl]piperidine, or a pharmaceutically acceptable salt or solvate thereof. In another embodiment, the present invention is directed toward a pharmaceutical composition for inhibiting the abnormal growth of cells comprising an effective amount of the tricyclic compound in combination with a pharmaceutically acceptable carrier.

In another embodiment, the present invention is directed toward a method for inhibiting the abnormal growth of cells, including transformed cells, comprising administering an effective amount of a tricylic compound to a mammal (e.g., a human) in need of such treatment. Abnormal growth of cells refers to cell growth independent of normal regulatory mechanisms (e.g., loss of contact inhibition). This includes the abnormal growth of: (1) tumor cells (tumors) expressing an activated Ras oncogene; (2) tumor cells in which the Ras protein is activated as a result of oncogenic mutation in another gene; (3) benign and malignant cells of other proliferative diseases in which aberrant Ras activation occurs, and (4) benign or malignant cells that are activated by mechanisms other than the Ras protein. Without wishing to be bound by theory, it is believed that these compounds may function either through the inhibition of G-protein function, such as ras p21, by blocking G-protein isoprenylation, thus making them useful in the treatment of proliferative diseases such as tumor growth and cancer, or through inhibition of ras farnesyl protein transferase, thus making them useful for their antiproliferative activity against ras transformed cells.

The cells to be inhibited can be tumor cells expressing an activated ras oncogene. For example, the types of cells that may be inhibited include pancreatic tumor cells, lung cancer cells, myeloid leukemia tumor cells, thyroid follicular tumor cells, myelodysplastic tumor cells, epidermal carcinoma tumor cells, bladder carcinoma tumor cells or colon tumors cells. Also, the inhibition of the abnormal growth of cells by the treatment with a tricyclic compound may be by inhibiting ras farnesyl protein transferase. The inhibition may be of tumor cells wherein the Ras protein is activated as a result of oncogenic mutation in genes other than the Ras gene. Alternatively, the tricyclic compounds may inhibit tumor cells activated by a protein other than the Ras protein.

This invention also provides a method for inhibiting tumor growth by administering an effective amount of a tricyclic compound to a mammal (e.g., a human) in need of such treatment. In particular, this invention provides a method for inhibiting the growth of tumors expressing an activated Ras oncogene by the administration of an effective amount of the above described compounds. Examples of tumors which may be inhibited include, but are not limited to, lung cancer (e.g., lung adenocarcinoma), pancreatic cancers (e.g., pancreatic carcinoma such as, for example, exocrine pancreatic carcinoma), colon cancers (e.g., colorectal carcinomas, such as, for example, colon adenocarcinoma and colon adenoma), myeloid leukemias (for example, acute myelogenous leukemia (AML)), thyroid follicular cancer, myelodysplastic syndrome (MDS), bladder carcinoma and epidermal carcinoma.

It is believed that this invention also provides a method for inhibiting proliferative diseases, both benign and malignant, wherein Ras proteins are aberrantly activated as a result of oncogenic mutation in other genes—i.e., the Ras gene itself is not activated by mutation to an oncogenic form—with said inhibition being accomplished by the administration of an effective amount of the tricylic compounds described herein, to a mammal (e.g., a human) in need of such treatment. For example, the benign proliferative disorder neurofibromatosis, or tumors in which Ras is activated due to mutation or overexpression of tyrosine kinase oncogenes (e.g., neu, src, abl, lck, and fyn), may be inhibited by the tricyclic compounds described herein.

In another embodiment, the present invention is directed toward a method for inhibiting ras farnesyl protein transferase and the farnesylation of the oncogene protein Ras by administering an effective amount of the tricyclic compound to mammals, especially humans. The administration of the compounds of this invention to patients, to inhibit farnesyl protein transferase, is useful in the treatment of the cancers described above.

DETAILED DESCRIPTION OF THE INVENTION

As used herein, the following terms are used as defined below unless otherwise indicated:

$M^+$-represents the molecular ion of the molecule in the mass spectrum;

$MH^+$-represents the molecular ion plus hydrogen of the molecule in the mass spectrum;

Bu-represents butyl;

Et-represents ethyl;

Me-represents methyl;

Ph-represents phenyl;

The following solvents and reagents are referred to herein by the abbreviations indicated: tetrahydrofuran (THF); ethanol (EtOH); methanol (MeOH); acetic acid (HOAc or AcOH); ethyl acetate (EtOAc); N,N-dimethylformamide (DMF); trifluoroacetic acid (TFA); trifluoroacetic anhydride (TFAA); 1-hydroxybenzotriazole (HOBT); m-chloroperbenzoic acid (MCPBA); triethylamine ($Et_3N$); diethyl ether ($Et_2O$); ethyl chloroformate ($ClCO_2Et$); and 1-(3-dimethylaminopropyl)-3-ethyl carbodiimide hydrochloride (DEC).

Reference to the position of the substituents $R^1$, $R^2$, $R^3$, and $R^4$ is based on the numbered ring structure:

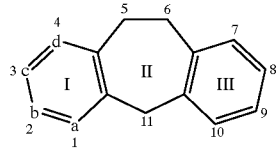

Certain compounds of the invention may exist in different stereoisomeric forms (e.g., enantiomers and diastereoisomers). The invention contemplates all such stereoisomers both in pure form and in mixture, including racemic mixtures. For example, the carbon atom at the C-11 position can be in the S or R stereoconfiguration.

Certain tricyclic compounds will be acidic in nature, e.g. those compounds which possess a carboxyl or phenolic hydroxyl group. These compounds may form pharmaceutically acceptable salts. Examples of such salts may include sodium, potassium, calcium, aluminum, gold and silver salts. Also contemplated are salts formed with pharmaceutically acceptable amines such as ammonia, alkyl amines, hydroxyalkylamines, N-methylglucamine and the like.

Certain basic tricyclic compounds also form pharmaceutically acceptable salts, e.g., acid addition salts. For example, the pyrido-nitrogen atoms may form salts with strong acid, while compounds having basic substituents such as amino groups also form salts with weaker acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous NaOH, potassium carbonate, ammonia and sodium bicarbonate. The free base forms differ from their respective salt forms somewhat in certain physical properties, such as solubility in polar solvents, but the acid and base salts are otherwise equivalent to their respective free base forms for purposes of the invention.

All such acid and base salts are intended to be pharmaceutically acceptable salts within the scope of the invention and all acid and base salts are considered equivalent to the free forms of the corresponding compounds for purpoposes of the invention.

Tricyclic compounds of fomula 1.0 can be isolated from the reaction mixture using conventional procedures, such as, for example, extraction of the reaction mixture from water with organic solvents, evaporation of the organic solvents, followed by chromatography on silica gel or other suitable chromatographic media.

Compounds of the present invention and preparative starting materials therof, are exemplified by the following examples, which should not be construed as limiting the scope of the disclosure.

EXAMPLE 1

4-[8-Chloro-3,7-dibromo-5,6-dihydro-11H-benzo[5,6]cyclohepta[1,2-b]pyridin-11-yl]-1-(4-thiomorpholinylacetyl)piperidine

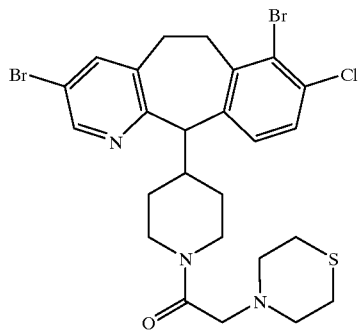

Step A:

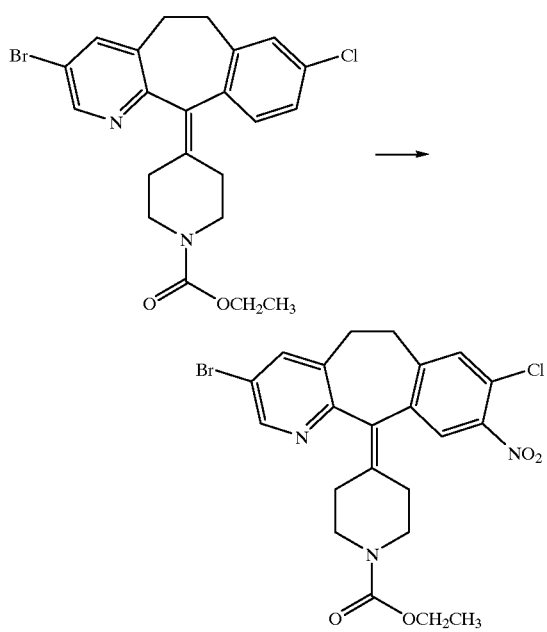

Combine 25.86 g (55.9 mmol) of 4-(8-chloro-3-bromo-5,6-dihydro-11 H-benzo[5,6]cyclohepta[1,2-b]pyridin-11-ylidene)-1-piperidine-1-carboxylic acid ethyl ester and 250 mL of concentrated $H_2SO_4$ at −5° C., then add 4.8 g (56.4 mmol) of $NaNO_3$ and stir for 2 hours. Pour the mixture into 600 g of ice and basify with concentrated $NH_4OH$ (aqueous). Filter the mixture, wash with 300 mL of water, then extract with 500 mL of $CH_2Cl_2$. Wash the extract with 200 mL of water, dry over $MgSO_4$, then filter and concentrate in vacuo to a residue. Chromatograph the residue (silica gel, 10% $EtOAc/CH_2Cl_2$) to give 24.4 g (86% yield) of the product. m.p.=165–167° C., Mass Spec.: $MH^+$=506, 508 (CI).

elemental analysis. calculated—C, 52.13; H, 4.17; N, 8.29. found—C, 52.18; H, 4.51; N, 8.16.

Step B:

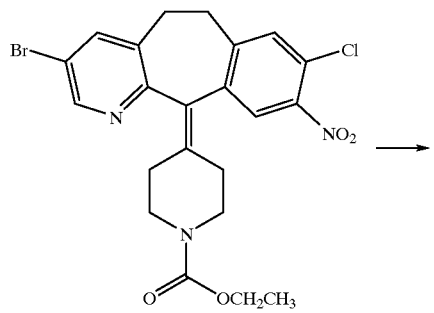

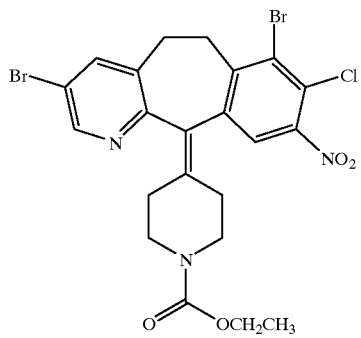

Combine 20 g (40.5 mmol) of the product of Step A and 200 mL of concentrated $H_2SO_4$ at 20° C., then cool the mixture to 0° C. Add 7.12 g (24.89 mmol) of 1,3-dibromo-5,5-dimethyl-hydantoin to the mixture and stir for 3 hours at 20° C. Cool to 0° C., add an additional 1.0 g (3.5 mmol) of the dibromohydantoin and stir at 20° C. for 2 hours. Pour the mixture into 400 g of ice, basify with concentrated $NH_4OH$ (aqueous) at 0° C., and collect the resulting solid by filtration. Wash the solid with 300 mL of water, slurry in 200 mL of acetone and filter to provide 19.79 g (85.6% yield) of the product. m.p.=236–237° C., Mass Spec.: $MH^+$=586 (CI).

elemental analysis: calculated—C, 45.11; H, 3.44; N, 7.17. found—C, 44.95; H, 3.57; N, 7.16

Step C:

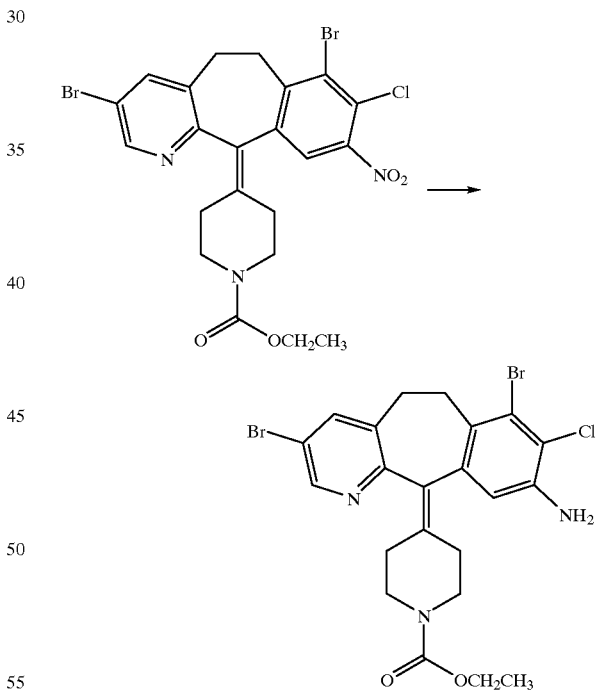

Combine 25 g (447 mmol) of Fe filings, 10 g (90 mmol) of $CaCl_2$ and a suspension of 20 g (34.19 mmol) of the product of Step B in 700 mL of 90:10 EtOH/water at 50° C. Heat the mixture at reflux overnight, filter through Celite® and wash the filter cake with 2×200 mL of hot EtOH. Combine the filtrate and washes, and concentrate in vacuo to a residue. Extract the residue with 600 mL of $CH_2Cl_2$, wash with 300 mL of water and dry over $MgSO_4$. Filter and concentrate in vacuo to a residue, then chromatograph (silica gel, 30% $EtOAc/CH_2Cl_2$) to give 11.4 g (60% yield) of the product. m.p.=211–212° C., Mass Spec.: MH+=556 (CI).

elemental analysis: calculated—C, 47.55; H, 3.99; N, 7.56. found—C, 47.45; H, 4.31; N, 7.49.

Step D:

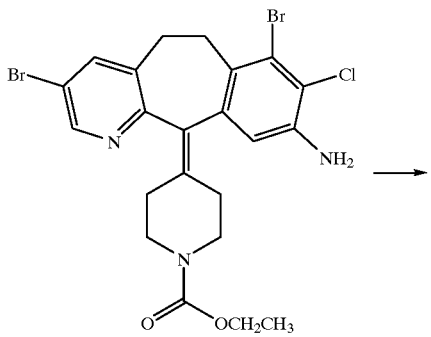

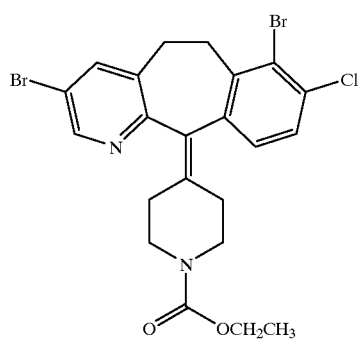

Slowly add (in portions) 20 g (35.9 mmol) of the product of Step C to a solution of 8 g (116 mmol) of NaNO$_2$ in 120 mL of concentrated HCl (aqueous) at −10° C. Stir the resulting mixture at 0° C. for 2 hours, then slowly add (dropwise) 150 mL (1.44 mole) of 50% H$_3$PO$_2$ at 0° C. over a 1 hour period. Stir at 0° C. for 3 hours, then pour into 600 g of ice and basify with concentrated NH$_4$OH (aqueous). Extract with 2×300 mL of CH$_2$Cl$_2$, dry the extracts over MgSO$_4$, then filter and concentrate in vacuo to a residue. Chromatograph the residue (silica gel, 25% EtOAc/hexanes) to give 13.67 g (70% yield) of the product. m.p.=163–165° C., Mass Spec.: MH+=541 (CI).

elemental analysis: calculated—C, 48.97; H, 4.05; N, 5.22. found—C, 48.86; H, 3.91; N, 5.18.

Step E:

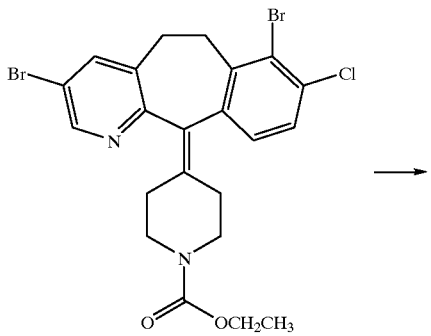

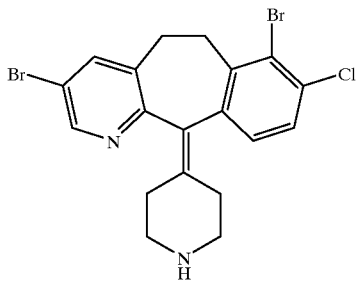

Combine 6.8 g (12.59 mmol) of the product of Step D and 100 mL of concentrated HCl (aqueous) and stir at 85° C. overnight. Cool the mixture, pour it into 300 g of ice and basify with concentrated NH$_4$OH (aqueous). Extract with 2×300 mL of CH$_2$Cl$_2$, then dry the extracts over MgSO$_4$. Filter, concentrate in vacuo to a residue, then chromatograph (silica gel, 10% MeOH/EtOAc+2% NH$_4$OH (aqueous)) to give 5.4 g (92% yield) of the title compound. m.p.= 172–174° C., Mass Spec.: MH+=469 (FAB).

elemental analysis: calculated—C, 48.69; H, 3.65; N, 5.97. found—C, 48.83; H, 3.80; N, 5.97.

Step F:

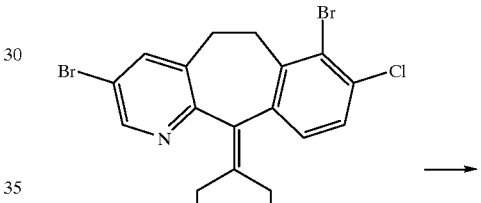

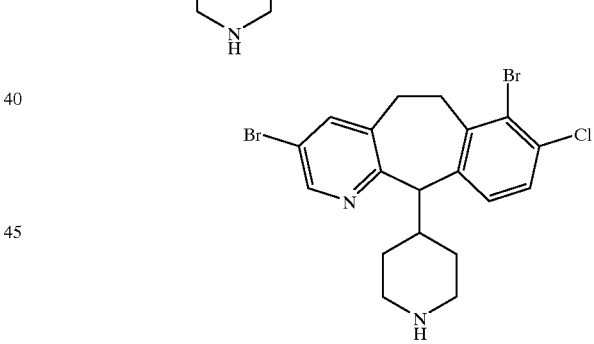

Combine 13 g (33.3 mmol) of the compound of Example 1, Step E, and 300 mL of toluene at 20° C., then add 32.5 mL (32.5 mmol) of a 1 M solution of DIBAL in toluene. Heat the mixture at reflux for 1 hr., cool to 20° C., add another 32.5 mL of 1 M DIBAL solution and heat at reflux for 1 hr. Cool the mixture to 20° C. and pour it into a mixture of 400 g of ice, 500 mL of EtOAc and 300 mL of 10% NaOH (aqueous). Extract the aqueous layer with CH$_2$Cl$_2$ (3×200 mL), dry the organic layers over MgSO$_4$, then concentrate in vacuo to a residue. Chromatograph (silica gel, 12% MeOH/ CH$_2$Cl$_2$+4% NH$_4$OH) to give 10.4 g of the title compound as a racemate. Mass Spec.: MH+=469/471 (FAB).

Step G.

4-[8-Chloro-3,7-dibromo-5,6-dihydro-11H-benzo[5,6] cyclohepta[1,2-b]pyridin-11-yl]-1-(hydroxyacetyl) piperidine

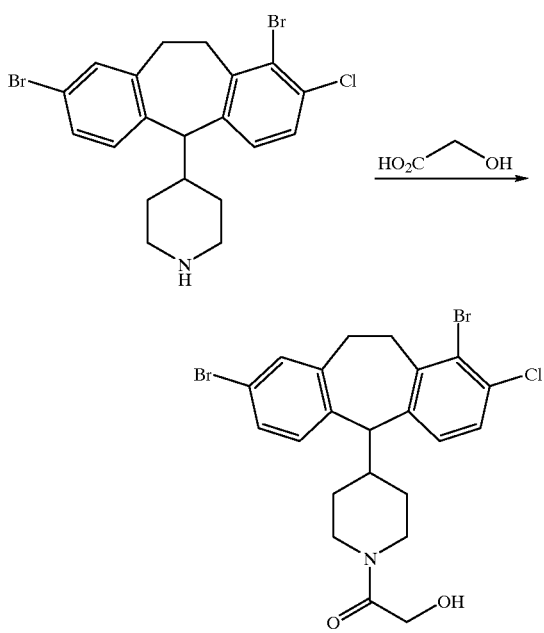

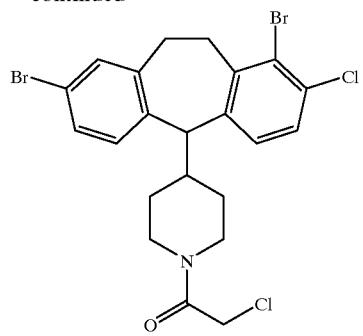

A mixture of the compound from Example 1, Step G (0.11 g; 0.2 mmoles) and 1.5 ml of thionyl chloride is stirred at ambient temperature for 18 hours and concentrated at reduced pressure. The residue is dissolved in $CH_2Cl_2$ and toluene is added to give a turbid solution which is concentrated again and then dried under high vacuum to give the title compound (0.11 g), a yellow puff.

MS: 547/549 (M/M+2).

Step I.

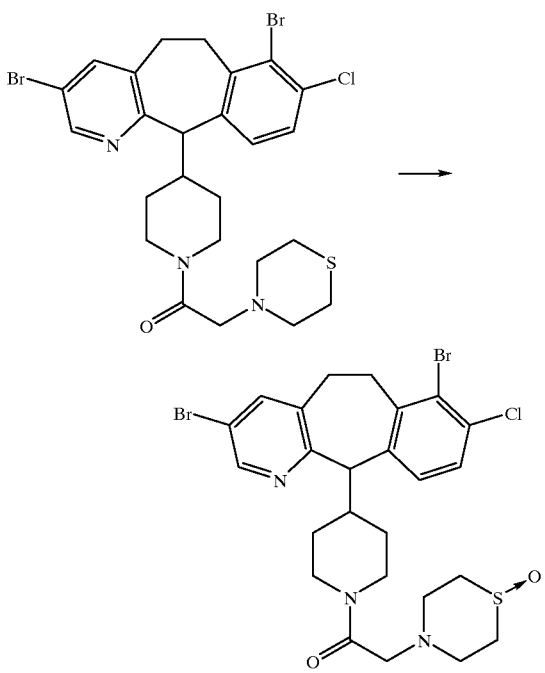

To a solution of 0.235 g of the material from Example 1, Step F (0.5 mmoles) in 3 ml of anhydrous Dimethylformamide (DMF) at ambient temperature is added 0.17 ml of N-Methylmorpholine (NMM), 0.075 g of 1-Hydroxybenzotriazole (HOBT), 0.145 g of 1-(3-Dimethylaminopropyl)-3-ethylcarbodiimide (DEC) and 0.06 g of 80% technical grade glycolic acid. The resulting yellow solution is stirred for 24 h and evaporated under high vacuum. The residue is partitioned between $CH_2Cl_2$ and saturated brine; the aqueous layer is extracted with $CH_2Cl_2$ (3×25 ml portions). The combined organic layer is dried over $Mg_2SO_4$, filtered and concentrated. The residue is purified by flash chromatography over 30 g of silica gel with 0.5 l each of 60% EtOAc/Hexane and 3% MeOH/$CH_2Cl_2$ to give the title compound (0.255 g, yield 96.5%).

MS: 529 (M+H).

Step H. 4-[8-Chloro-3,7-dibromo-5,6-dihydro-11H-benzo[5,6]cyclohepta[1,2-b]pyridin-11-yl]-1-(chloroacetyl)piperidine.

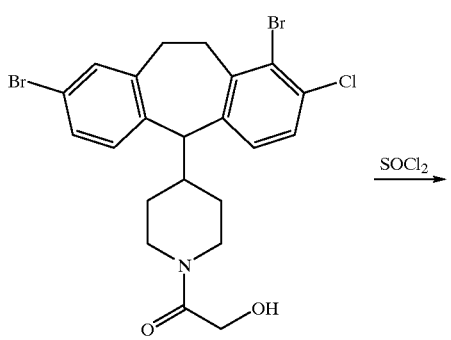

To a solution of ~0.11 g of 4-[8-Chloro-3,7-dibromo-5,6-dihydro-11H-benzo[5,6 ]cyclohepta[1,2-b]pyridin-11-yl]-1-(chloroacetyl)piperidine in 5 ml of $CH_2Cl_2$ is added 0.12 ml of thiomorpholine and the mixture is stirred at ambient temperature for 24 h, and diluted with 20 ml of distilled water. The layers are separated and the aqueous layer is back extracted with 10 ml of $CH_2Cl_2$. The combined organic layer is washed once with saturated brine, dried over $Mg_2SO_4$, filtered and evaporated to a brown residue. Flash chromatography over 20 g silica gel with 200 ml of 3% MeOH/$CH_2Cl_2$ gives 0.12 g of the title compound, yield in two steps is 93.8%. MS: 614.5 (M+H).

FPT $IC_{50}$=0.0089 $\mu$M.

EXAMPLE 2

4-[8-Chloro-3,7-dibromo-6,11-dihydro-5H-benzo[5,6]cyclohepta[1,2-b]pyridin-11-yl]-1-(4-thiomorpholinylacetyl)piperidine S-oxide

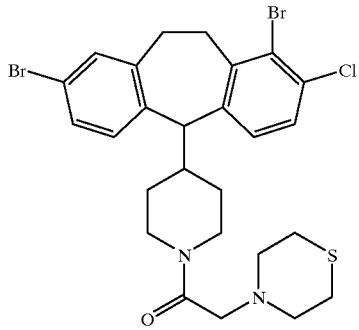

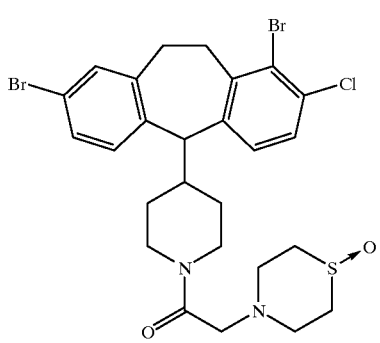

To a solution of 0.09 g of 4-[8-Chloro-3,7-dibromo-5,6-dihydro-11H-benzo [5,6]cyclohepta[1,2-b]pyridin-11-yl]-1-(4-thiomorpholinyl)piperidine from Example 1, Step 1 (0.15 mmoles) in 10 ml of distilled Tetrahydrofuran (THF) is added 123 microliters (µl) of trifluoroacetic acid (TFA) and 121 µl of 30% $H_2O_2$. The resulting solution is stirred at ambient temperature for 20 hours and concentrated. The residue is extracted with 2×10 ml portions of $CH_2Cl_2$ and 10 ml of distilled water. The combined organic layer is washed once with saturated brine, dried over $Mg_2SO_4$, filtered and evaporated to a colorless residue. Prep. TLC with 10% MeOH ($NH_3$)/$CH_2Cl_2$ gives 0.03 g of the title compound, white solid. Yield: 32.6%.

MS: 630 (M).

FPT $IC_{50}$=0.0068 µM.

EXAMPLE 3

(+,−)-1-(3-bromo-8,10-dichloro-5-ethyl-6,11-dihydro-5H-benzo[5,6]cyclohepta[1,2-b]pyridin-11-yl)-4-(4-pyridinylacetyl)piperazine N4-oxide

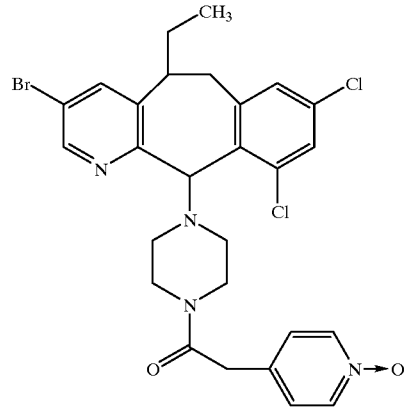

Step A.

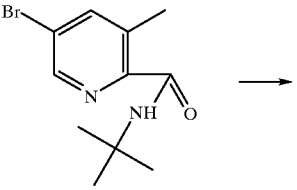

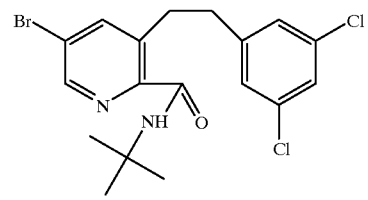

Add n-butyl lithium (2.5M in hexanes, 7.3 ml, 18,25 mmol) to a solution of diisopropylamine (2.8 ml, 20.13 mmol) in tetrahydrofuran (THF) (distilled; 20 ml) at −78° C. over a dry ice-acetone bath. Stir at 0° C. for 30 minutes then cool to −78° C. A solution of N-(1,1-dimethylethyl)-3-methyl-5-bromo-2-pyridinecarboxamide (2.0 g; 7.38 mmol) in THF (10 ml) is added at −78° C. and the resultant purple solution is stirred at −78° C. for a further half hour. A solution of 3,5 dichlorobenzyl choride (2.8 g; 14.32 mmol) in tetrahydrofuran (10 ml) is added dropwise at −78° C. Dry ice/acetone bath is replaced with ice/water bath, and the reaction mixture is stirred for 11/2 hours at 0° C. Thin layer chromatography (3% V/V Ethyl acetate: hexanes) determined completion of the reaction. The reaction mixture is quenched with water (100 ml) and extracted with ethyl acetate (2×200 ml portions). The organic layer is separated, washed with water (100 ml), dried over magnesium sulfate, filtered and the solvent evaporated to yield an oil which chromatographs on silica gel (3% V/V ethylacetate:hexanes) as a colorless oil which when pumped under high vacuum (0.2 mm), solidifies to a white solid (2.7 g, 96.7% yield).
Step B.

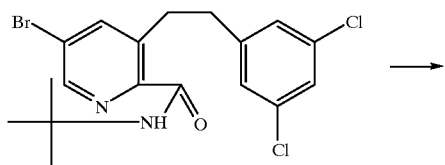

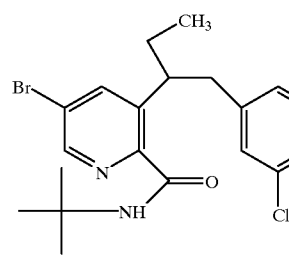

Add n-butyl lithium (2.5M in hexanes; 2.3 ml, 5.75 mmol) to a solution of diisopropylamine (0.82 ml, 5.86 mmol) in tetrahydrofuran (10 ml distilled over sodium) at −78° C. Stir for 20 minutes at −78° C. Add the product of Example 3, Step A (1.0 g; 2.64 mmol) in tetrahydrofuran (5 ml) and stir the purple solution for ½ hour at −78° C. Ethyl bromide (0.7 ml; 9.37 mmol) is added neat; the dry ice bath is replaced with an ice/water bath and the reaction is stirred for one hour at 0° C. Thin layer chromatography using silica gel (3% ethyl acetate; hexane) determined completeness of the reaction. Water (50 ml) and ethyl acetate (100 ml) are added to the reaction mixture. The organic layer separates, is washed with water (5 ml), dried over sodium sulfate, filtered and the solvent evaporated to give a pale yellow oil which chromatographs on silica gel (3% V/V ethyl acetate: hexane), which when pumped under high vacuum (0.2 mm) for 2 hours gives a colorless oil (0.95 g: 88.7% yield). Ms: Cl MH 459.
Step C.

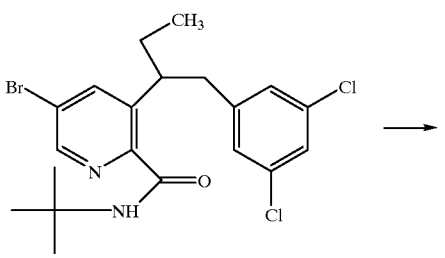

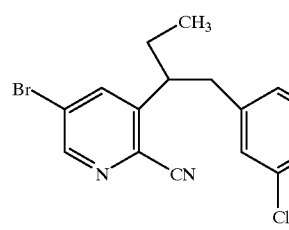

Add phosphorous oxychloride (5 ml, 53.6 mmol) to a solution of the product of Example 3, Step B (0.9 g, 1.96 mmol) in toluene (10 ml); then stir at reflux temperature for 5 hours. Th e reaction mixture is cooled to room temperature, and the solvent is evaporated under reduced pressure. Toluene (20 ml) is added, and the solvent is re-evaporated. Water (30 ml), ethyl acetate (100 ml) and 10% sodium hydroxide (10 ml) are added sequentially to the residual oil. The organic layer is separated, washed with brine (50 ml), dried over magnesium sulfate, filtered, and the solvent is evaporated, to give an oil which is used as such in the next reaction (0.8 g; 100% yield) Ms:Cl MH 383/385.
Step D.

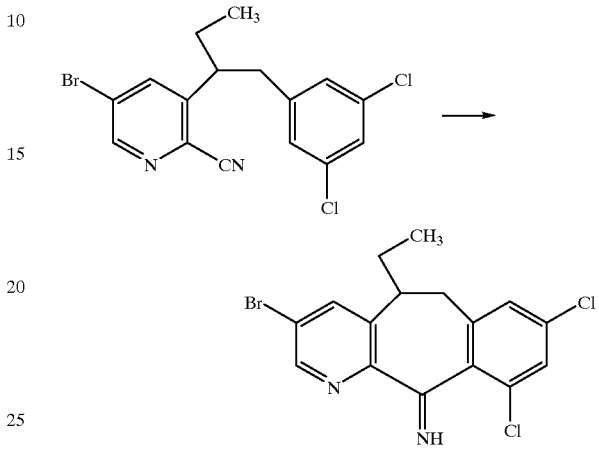

The product of Example 3, Step C (0.8 g; 2.08 mmol) and aluminum chloride (2.7 g; 20.2 mmol) are mixed at 20° C., then stirred over a preheated oil bath at 175° C. for 10 minutes. Thin layer chromatography using silica (1:1 V/V Ethyl acetate:hexanes) determines completion of the reaction. The reaction is cooled to 0° C., water (10 ml) is added, followed by 2 Normal (N) hydrochloric acid (15 ml). The mixture is made basic by addition of 20% sodium hydroxide with ice bath cooling, then extracted with methylene chloride (2×100 ml portions). The organic layer is separated, dried over magnesium sulfate, filtered, and the solvent evaporated to give a white solid (0.6 g; 75% yield). Ms: Cl MH (383/385)
Step E.

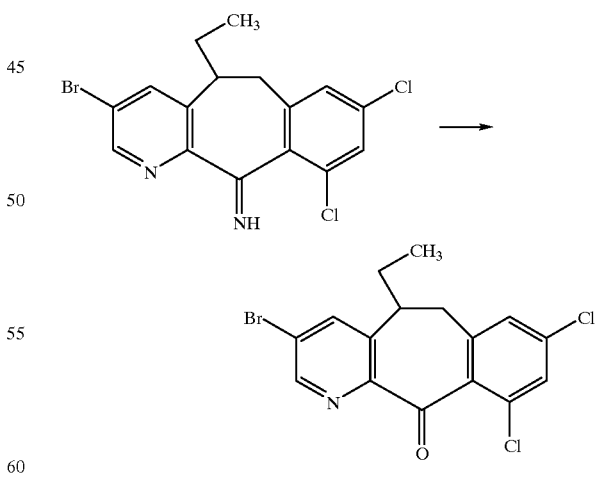

A solution of the product from Example 3, Step D (0.3 g 7.79×10$^{-4}$ m) in 6 N hydrochloric acid (10 ml) and methanol (5 ml) is stirred for 24 hours at reflux temperature. The reaction is cooled to 20° C., added to ice (100 g) and made basic to pH 14 with 25% sodium hydroxide at 0° C. The white solid precipitate is collected, washed with water (20 ml), dissolved in CH$_2$Cl$_2$ (100 ml) dried over magnesium sulfate, filtered and the solvent evaporated. The residual solid chromotographs on silica gel (1:1 V/V ethyl acetate:hexanes) to give a white solid (200 mg; 66% yield). Ms: Cl MH (384/386).

Step F.

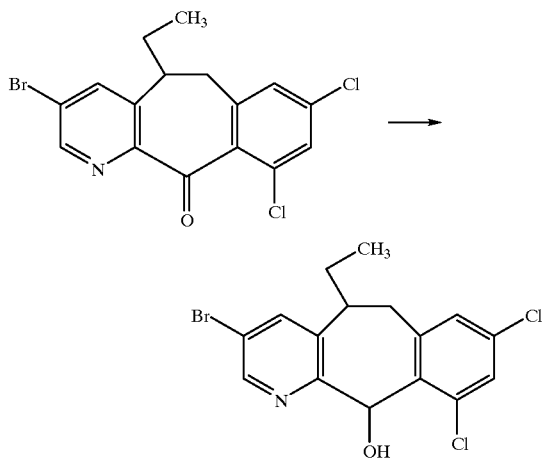

Sodium borohydride (100 mg; 2.66 mmol) is added to a solution of the product from Example 3, Step E (130 mg; 0.338 mmol) in ethanol (5 ml) at 0° C. and the reaction mixture is stirred for 5 minutes. Thin layer chromatography (silica gel; 30% V/V EtoAc:hexane) is used to determine completion of the reaction. Water (20 ml), and methylene chloride (30 ml) are added, the organic layer is separated, dried over magnesium sulfate, filtered and the solvent evaporated to give an oil which chromatographs on silica gel (20% V/V ethylacelate:hexanes), a 70:30 mixture of 2 diastereomers (130 mg; 100% yield). MS: Cl (MH 388).

Step G.

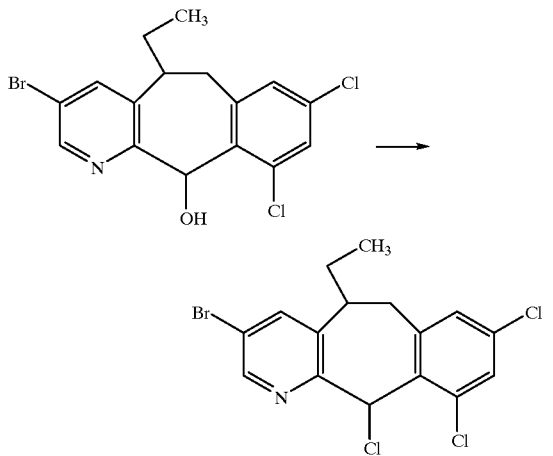

Thionyl chloride (0.15 ml; 2.05 mmol) is added to a solution of the product from Example 3, Step F (60 mg; 0.155 mmol) in toluene (3 ml) at 0° C. The reaction mixture is stirred at 0° C. for 1 hour and at 20° C. for an additional hour. The reaction is cooled to 0° C., water (10 ml) ethyl acetate (20 ml) and 10% sodium hydroxide (5 ml) are sequentially added. The organic layer is separated, washed with brine (15 ml), dried over magnesium sulfate, filtered and the solvent evaporated to give an oil (65 mg).

Step H.

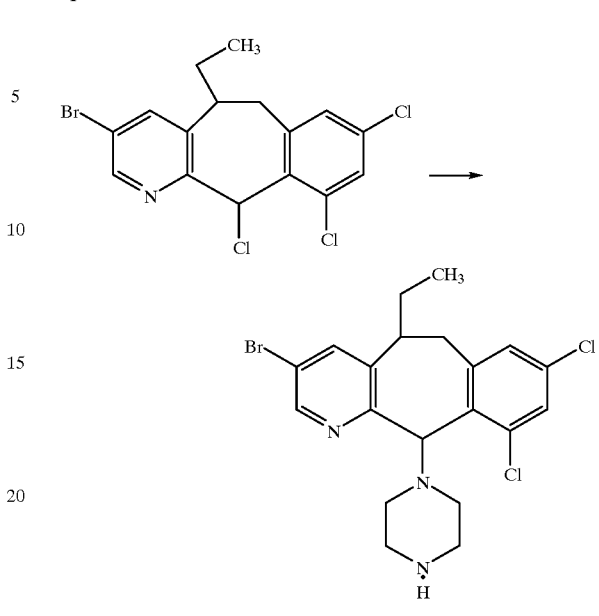

Piperazine (100 mg; 1.16 mmol) is added to a solution of the product from Example 3, Step G (60 mg; 0.155 mmol) in acetontrile (5 ml) at 0° C. Triethylamine (0.2 ml; 1.43 mmol) is added, and the reaction mixture is stirred at 20° C. for 2 hours. Water (20 ml) and methylene chloride (50 ml) are added. The organic layer is separated, washed with brine (20 ml), dried over magnesium sulfate, filtered, and the solvent is evaporated to the crude product as a white solid (60 mg) Ms: Cl MH (456). NMR shows 2 diastereomers in an 80/20 mix Step I.

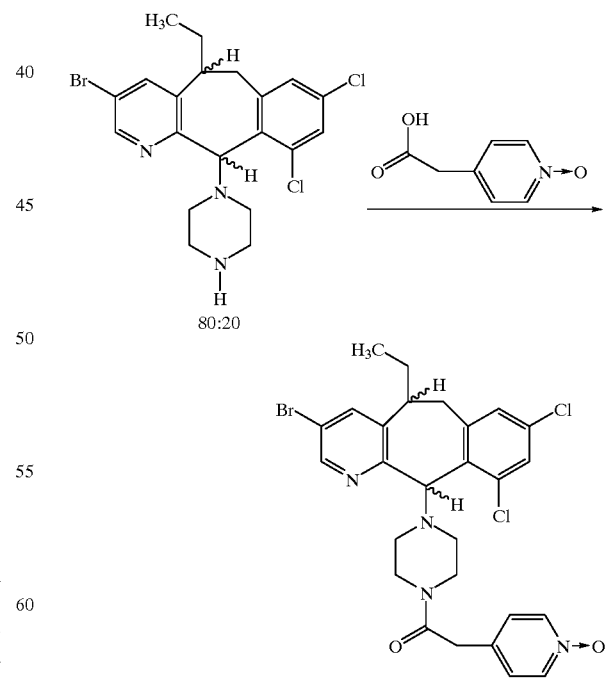

Add 1-hydroxybenzotriazole (40 mg, 0.296 mmol), 1-(3-dimethylaminopropyl)-3-ethyl carbodiimide hydrochloride (EDCl) (50 mg, 0.26 mmol) and 4-pyridyl N-oxide acetic acid (40 mg; 0.26 mmol) to a solution of the product from Example 3, Step H (50 mg; 0.109 mmol) in dimethyl formamide (5 ml) at 0° C., N-methyl morpholine (0.5 ml, 4.03 mmol) is added, and the reaction mixture is stirred for 24 hours at 20° C. The solvent is evaporated under reduced pressure, the residual oil is extracted with methylene chloride (40 ml) washed with water (20 ml) and brine (20 ml), dried over magnesium sulfate, filtered, and solvent evaporated to give an oil which chromatographs on silica gel (10% V/V methanol:methylene chloride) yielding product as white solid, dried under high vacuum (0.2 mm) for 3 hours (50 mg; 78% yield).

NMR: an 80:20 mix of diastereomers.

Ms FABS MH 590.8/588.9

Exact Mass: $C_{27}H_{26}N_4O_2BrCl_2$

Calculated MH$^+$587.0616; Measured 587.0612

Step 3J. Separation of Diastereomers

The mixture of the 2 Diastereomers (200 mg; 80:20 mix) are separated on a Chiralpack AD column from Chiral Technologies Inc., Exton, Pa. using ethanol as the eluting solvent. Chiralpack AD is amylose tris (3,5-dimethylphenyl carbamate) coated on a 10 μm silica gel substrate.

1) The major diastereomer (120 mg) is obtained as a racemate, a white solid

FABS MH 588.9/590.8

FABS MS Calculated MH+ $C_{27}H_{26}N_4O_2BrCl_2$ 587.0616

Measured MH+ 587.0612

FPT IC$_{50}$=0.006 μM.

2) The minor diastereomer (20 mg) is obtained as a racemate, a white solid

MS FABS 588.9/590.8

EXAMPLE 4

(+)-4-(3-Bromo-8,10-dichloro-6,11-dihydro-5H-enzo[5,6]cyclohepta[1,2-b]pyridin-11-yl)-1-[2-(1,3-dihydro-1,3-dioxo-2H-isoindol-2-yl)-1-oxoethyl] piperidine

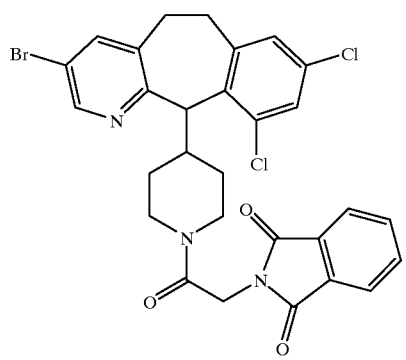

Step A:

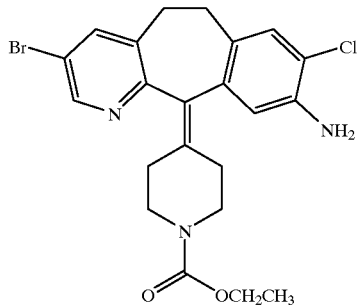

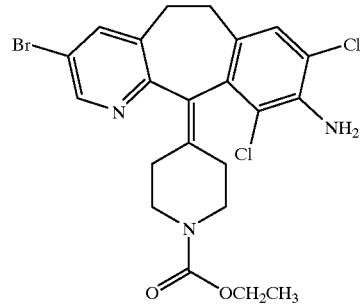

Dissolve 9.90 g (18.9 mmol) of the product of Example 5, Step B, in 150 mL CH$_2$Cl$_2$ and 200 mL of CH$_3$CN and heat to 60° C. Add, 2.77 g (20.8 mmol) N-chlorosuccinimide and heat to reflux for 3 h., monitoring the reaction by TCL (30%EtOAc/H$_2$O). Add an additional 2.35 g (10.4 mmol) of N-chlorosuccinimide and reflux an additional 45 min. Cool the reaction mixture to room temperature and extract with 1N NaOH and CH$_2$Cl$_2$. Dry the CH$_2$Cl$_2$ layer over MgSO$_4$, filter and purify by flash chromatography (1200 mL normal phase silica gel, eluting with 30% EtOAc/H$_2$O) to obtain 6.24 g of the desired product. M.p. 193–195.4° C.

Step B:

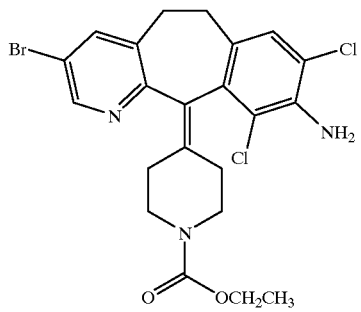

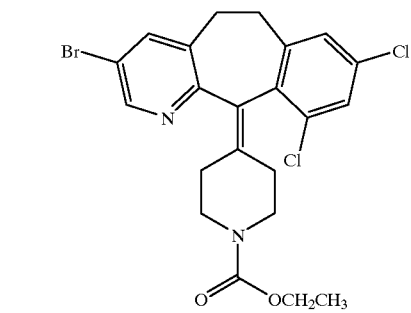

To 160 mL of conc. HCl at −10° C. add 2.07 g (30.1 mmol) NaNO$_2$ and stir for 10 min. Add 5.18 g (10.1 mmol)

of the product of Example 4, Step A and warm the reaction mixture from −10° C. to 0° C. for 2 h. Cool the reaction to −10° C., add 100 mL H$_3$PO$_2$ and let stand overnight. To extract the reaction mixture, pour over crushed ice and basifiy with 50% NaOH/CH$_2$Cl$_2$. Dry the organic layer over MgSO$_4$, filter and concentrate to dryness. Purify by flash chromatography (600 mL normal phase silica gel, eluting with 20% EtOAc/hexane) to obtain 3.98 g of product. Mass spec.: MH$^+$=497.2.

Step C:

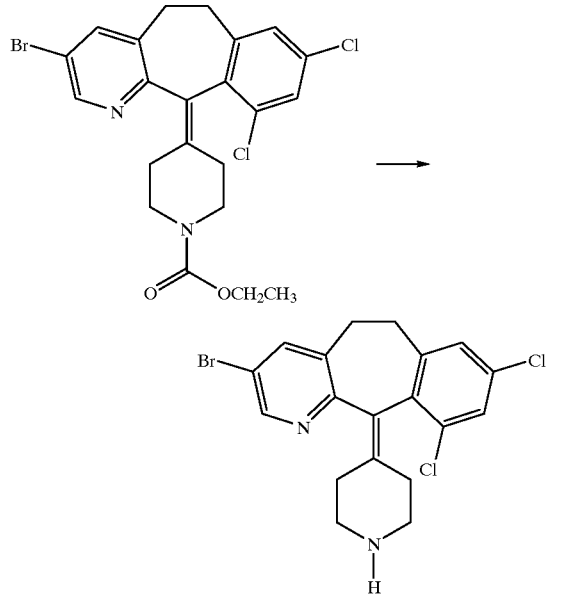

Dissolve 3.9 g of the product of Example 4, Step B in 100 mL conc. HCl and reflux overnight. Cool the mixture, basify with 50% w/w NaOH and extract the resultant mixture with CH$_2$Cl$_2$. Dry the CH$_2$Cl$_2$ layer over MgSO$_4$, evaporate the solvent and dry under vacuum to obtain 3.09 g of the desired product. Mass spec.: MH$^+$=424.9.

Step D:

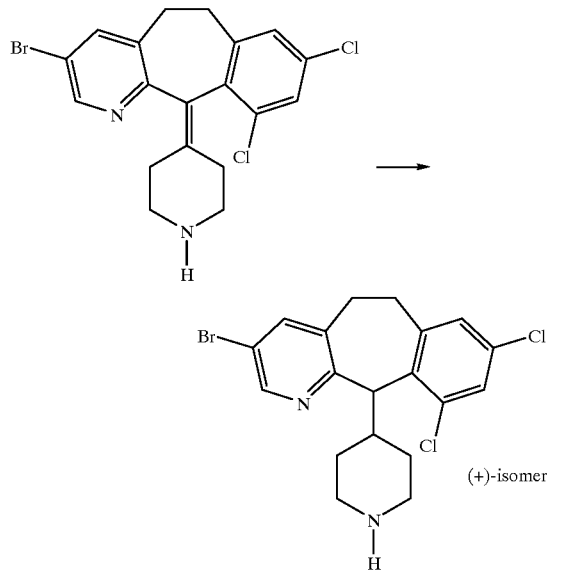

Using a procedure similar to that described in Example 5, Steps F&G obtain 1.73 g of the desired product, m.p. 169.6–170.1° C.; $[\alpha]_D^{25}$=+48.2° (c=1, MeOH).

Step E.

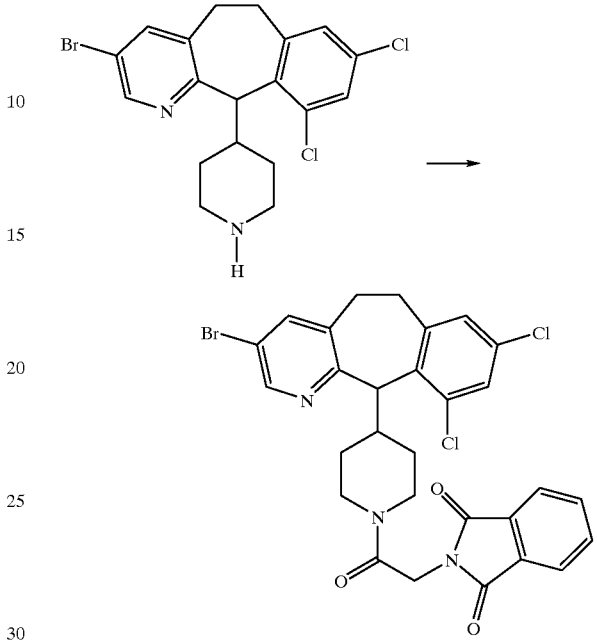

Dissolve product of Example 5, Step D in 10 mL DMF 0.5 g (1.2 mmol), add 0.3 g (1.5 mmol) of pthaloylglycine, 0.29 g (1.5 mmol) of DEC, 0.20 g (1.5 mmol) of HOBT and 0.15 g (1.5 mmol) N-methyl morpholine at ~0° C. Stir the reaction mixture overnight letting it warm to room temperature. Remove all the volatiles. Partition it between H$_2$O—CH$_2$Cl$_2$. Extract the aqueous phase with CH$_2$Cl$_2$. Combine the CH$_2$Cl$_2$ fractions and dry over MgSO$_4$ and concentrate. Purify by flash chromatography using 50% EtOAc-Hexane to obtain the title compound. Mass Spec. MH$^+$=614 mp=144–145° C.

FPT IC$_{50}$=0.0186 $\mu$M.

EXAMPLE 5

(+)-4-(3,10-Dibromo-8-chloro-6,11-dihydro-5H-benzo[5,6]cyclohepta[1,2-b]pyridin-11 (R)-yl)-1-[(1-oxopropyl-4-piperidinyl)acetyl]piperidine Step A:

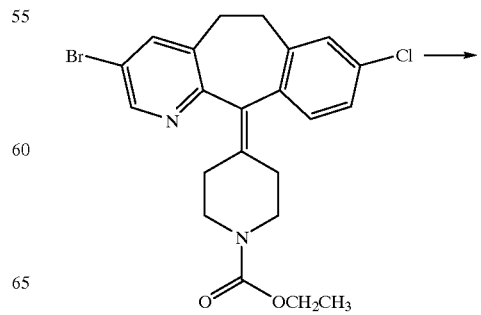

-continued

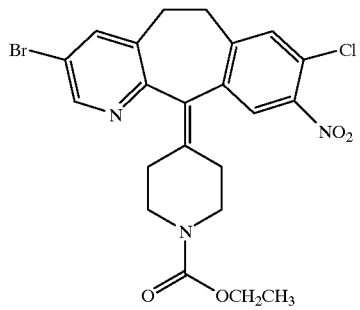

Combine 15 g (38.5 mmol) of 4-(8-chloro-3-bromo-5,6-dihydro-11H-benzo[5,6]cyclohepta[1,2-b]pyridin-11-ylidene)-1-piperidine-1-carboxylic acid ethyl ester and 150 mL of concentrated $H_2SO_4$ at $-5°$ C., then add 3.89 g (38.5 mmol) of $KNO_3$ and stir for 4 hours. Pour the mixture into 3 L of ice and basify with 50% NaOH (aqueous). Extract with $CH_2Cl_2$, dry over $MgSO_4$, then filter and concentrate in vacuo to a residue. Recrystallize the residue from acetone to give 6.69 g of the product. $^1$H NMR ($CDCl_3$, 200 MHz): 8.5 (s, 1H); 7.75 (s, 1H); 7.6 (s, 1H); 7.35 (s, 1H); 4.15 (q, 2H); 3.8 (m, 2H); 3.5–3.1 (m, 4H); 3.0–2.8 (m, 2H); 2.6–2.2 (m, 4H); 1.25 (t, 3H).

Step B:

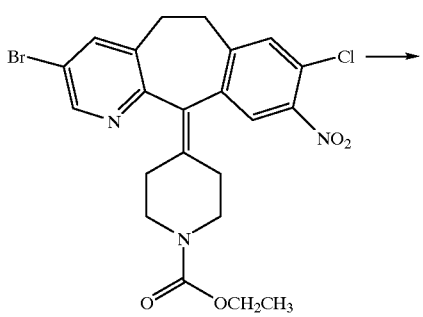

Combine 6.69 g (13.1 mmol) of the product of Step A and 100 mL of 85% EtOH/water, then add 0.66 g (5.9 mmol) of $CaCl_2$ and 6.56 g (117.9 mmol) of Fe and heat the mixture at reflux overnight. Filter the hot reaction mixture through celite® and rinse the filter cake with hot EtOH. Concentrate the filtrate in vacuo to give 7.72 g of the product. Mass Spec.: MH$^+$=478.0

Step C:

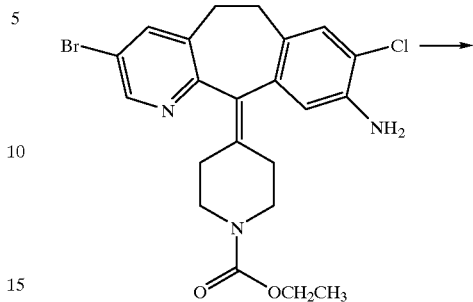

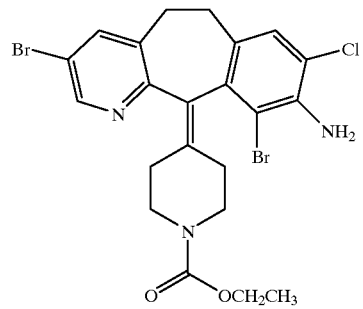

Combine 7.70 g of the product of Step B and 35 mL of HOAc, then add 45 mL of a solution of $Br_2$ in HOAc and stir the mixture at room temperature overnight. Add 300 mL of 1 N NaOH (aqueous) then 75 mL of 50% NaOH (aqueous) and extract with EtOAc. Dry the extract over MgSO and concentrate in vacuo to a residue. Chromatograph the residue (silica gel, 20%–30% EtOAc/hexane) to give 3.47 g of the product (along with another 1.28 g of partially purified product). Mass Spec.: MH$^+$=555.9.

$^1$H NMR ($CDCl_3$, 300 MHz): 8.5 (s, 1H); 7.5 (s, 1H); 7.15 (s, 1H); 4.5 (s, 2H); 4.15 (m, 3H); 3.8 (br s, 2H); 3.4–3.1 (m, 4H); 9–2.75 (m, 1H); 2.7–2.5 (m, 2H); 2.4–2.2 (m, 2H); 1.25 (m, 3H).

Step D:

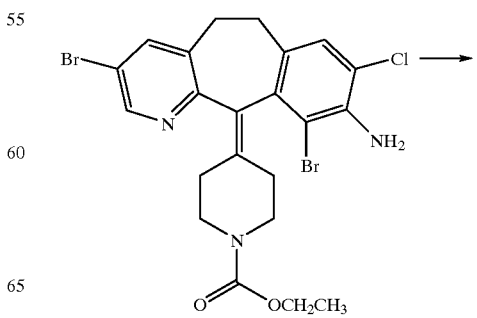

-continued

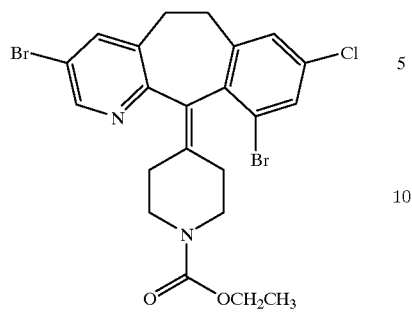

To 300 mL of HCl (cooled to −10° C.) is added sodium nitrite (NaNO$_2$) (1.86 g, 27 mmol) and stirred for 5 min. To this mixture is added portionwise the compound of Example 5, Step C (5 g, 9 mmol) over a period of 10 min. The reaction is allowd to warm up to 0–3° C. and stirred for 2 h. To this mixture is slowly added 75 mL of hypophosphonic acid and the reaction mixture is kept in a refrigerator for ∼16 hr. The mixture is poured into ice and the pH adjusted to between 9–10 with 50% (v/v) NaOH. Extraction is effected using ethyl acetate (EtOAc). The ethyl acetate is dried and concentrated in vacuo to a residue. Chromatograph the residue (silica gel, 10%–20% EtOAc/hexane) to give 3.7 g of the product. Mass Spec.: MH$^+$=541.0.

$^1$H NMR (CDCl$_3$, 200 MHz): 8.52 (s, 1H); 7.5 (d, 2H); 7.2 (s, 1H); 4.15 (q, 2H); 3.9–3.7 (m, 2H); 3.5–3.1 (m, 4H); 3.0–2.5 (m, 2H); 2.4–2.2 (m, 2H); 2.1–1.9 (m, 2H); 1.26 (t, 3H).

Step E:

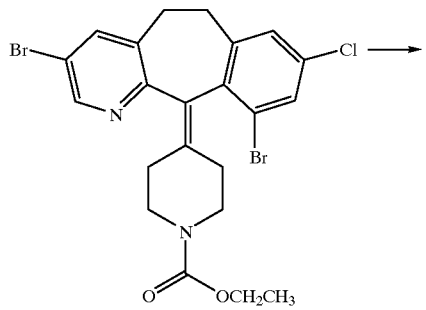

-continued

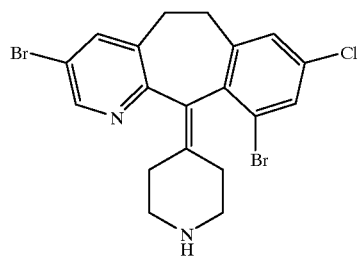

Combine 0.70 g (1.4 mmol) of the product of Step D and 8 mL of concentrated HCl (aqueous) and heat the mixture at reflux overnight. Add 30 mL of 1 N NaOH (aqueous), then 5 mL of 50% NaOH (aqueous) and extract with CH$_2$Cl$_2$. Dry the extract over MgSO$_4$ and concentrate in vacuo to give 0.59 g of the title compound. Mass Spec.: M$^+$=468.7. m.p.=123.9°–124.2° C.

Step F:

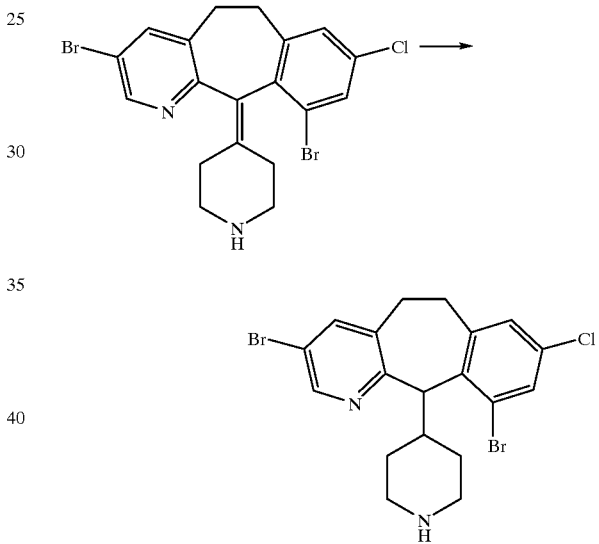

Prepare a solution of 8.1 g of the compound from Example 5, Step E in toluene and add 17.3 mL of a 1M solution of DIBAL in toluene. Heat the mixture at reflux and slowly add (dropwise) another 21 mL of 1 M DIBAL/toluene solution over a period of 40 min. Cool the reaction mixture to about 0° C. and add 700 mL of 1 M HCl (aqueous). Separate and discard the organic phase. Wash the aqueous phase with CH$_2$Cl$_2$, discard the extract, then basify the aqueous phase by adding 50% NaOH (aqueous). Extract with CH$_2$Cl$_2$, dry the extract over MgSO$_4$ and concentrate in vacuo to give 7.30 g of the title compound, which is a racemic mixture of enantiomers.

Step G—Separation of Enantiomers:

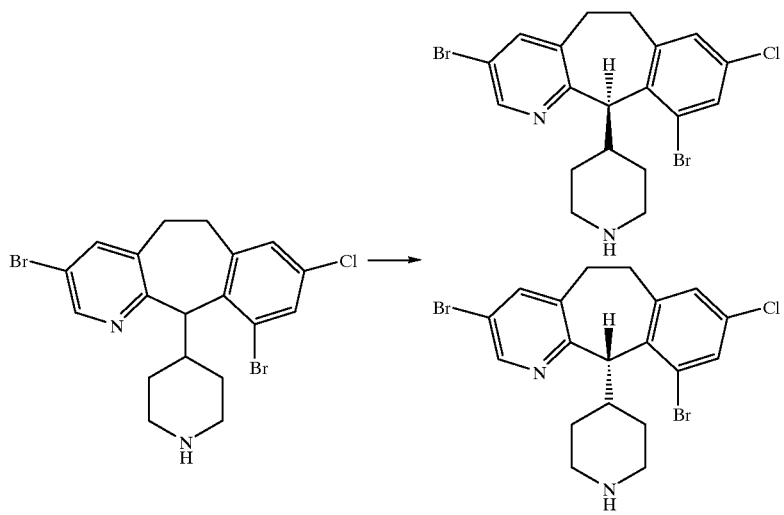

The racemic title compound of Example 5, Step F is separated by preparative chiral chromatography (Chiralpack AD, 5 cm×50 cm column, using 20% iPrOH/hexane+0.2% diethylamine), to give the (+)-isomer and the (−)-isomer of the above compounds.

Physical chemical data for (+)-isomer: m.p.=148.8° C.; Mass Spec. MH$^+$=472; $[\alpha]_D^{25}$=+65.6° (12.9 mg/2 mL MeOH).

Physical chemical data for (−)-isomer: m.p.=112° C.; Mass Spec. MH$^+$=472; $[\alpha]_D^{25}$=−65.2° (3.65 mg/2 mL MeOH).

Step H:

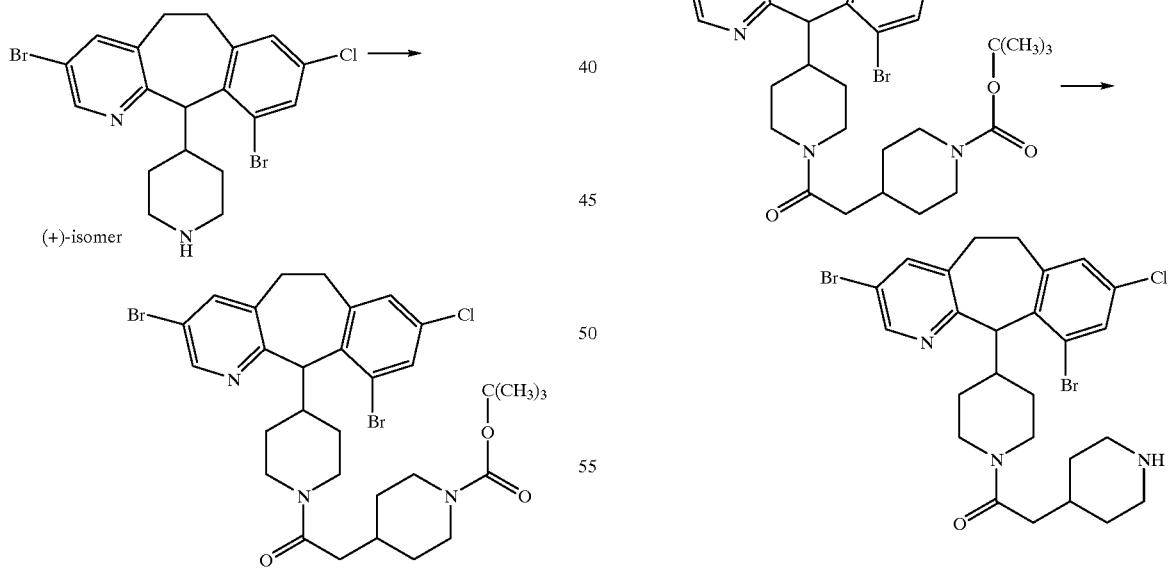

Combine 3.21 g (6.80 mmol) of the (+)-isomer product of Example 5, Step G and 150 mL of anhydrous DMF. React 1.33 g of the (+)-isomer with 1.37 g of 1-N-t-butoxy-carbonylpiperidinyl-4-acetic acid 1.69 g (8.8 mmol) of DEC, 1.19 g (8.8 mmol) of HOBT and 0.97 mL (8.8 mmol) of N-methylmorpholine and stir the mixture at room temperature overnight. Concentrate in vacuo to remove the DMF and add 50 mL of saturated NaHCO$_3$ (aqueous). Extract with CH$_2$Cl$_2$ (2×250 mL), wash the extracts with 50 mL of brine and dry over MgSO$_4$. Concentrate in vacuo to a residue and chromatograph (silica gel, 2% MeOH/ CH$_2$Cl$_2$+10% NH$_4$OH) to give 2.78 g of the product. Mass Spec.: MH$^+$=694.0 (FAB); $[\alpha]_D^{25}$=+34.1° (5.45 mg/2 mL, MeOH).

Step I:

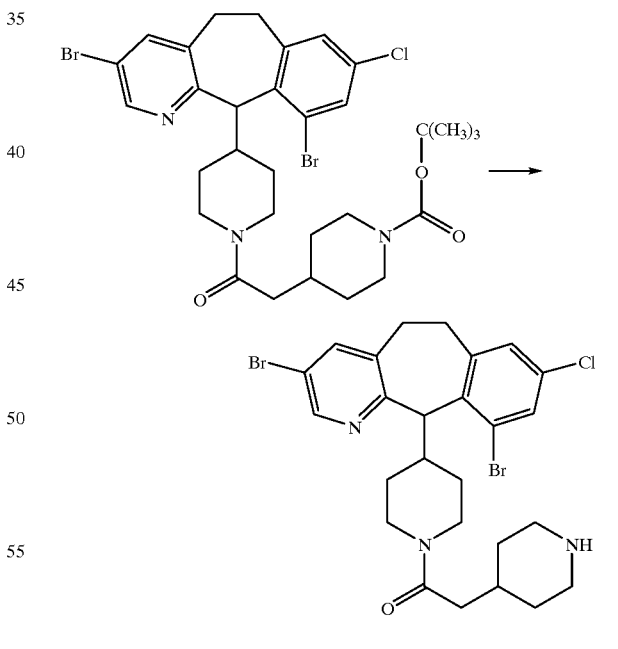

Treat 2.78 g of the compound of Example 5, Step H and 60 mL of CH$_2$Cl$_2$, then cool to 0° C. and add 55 mL of TFA. Stir the mixture for 3 h at 0° C., then add 500 mL of 1 N NaOH (aqueous) followed by 30 mL of 50% NaOH (aqueous). Extract with CH$_2$Cl$_2$, dry over MgSO$_4$ and concentrate in vacuo to to give 1.72 g of the product. m.p.=104.1° C.; Mass Spec.: M$^+$=597; $[\alpha]_D^{25}$=+53.4° (11.4 mg/2 mL, MeOH).

Step J.

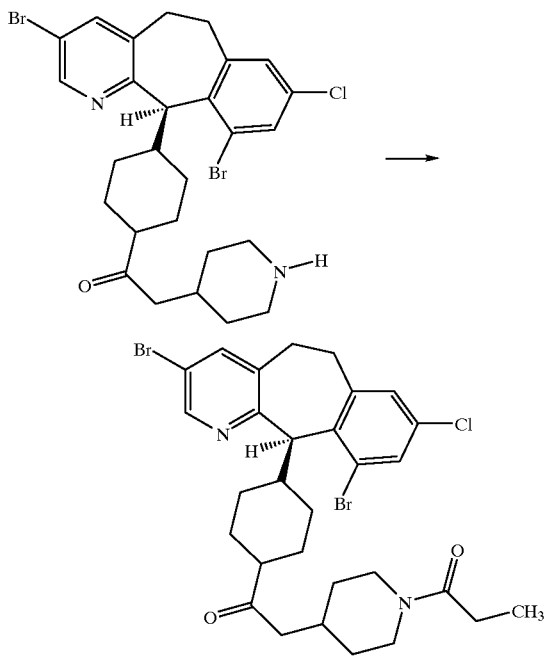

To the compound of Example 5, Step I (0.11 g, 0.19 mmol) and triethylamine (0.08 mL, 0.57 mmol) dissolved in anhydrous dichloromethane (6 mL) is added propionyl chloride (0.04 mL, 2 eq). After stirring at room temperature overnight, 1 M hydrochloric acid is added and the mixture is shaken. The organic phase is separated and washed with 1 N aqueous sodium hydroxide then dried over anhydrous magnesium sulfate. Filtration and concentration in vacuo affords the title compound (0.10 g, 83% yield, mp 106.4–109.3° C.).

FPT $IC_{50}$=0.0068 $\mu$M.

PREPARATION OF STARTING MATERIALS

Starting materials useful in preparing the compounds of the present invention are exemplified by the following preparative examples, which should not be construed to limit the scope of the disclosure. Such starting materials can be prepared using known methods in the art, such as taught in See J. K. Wong et al., Bioorganic & Medicinal Chemistry Letters, Vol. 3, No. 6, pp. 1073–1078, (1993); U.S. Pat. Nos. 5,089,496; 5,151,423; 4,454,143; 4,355,036; PCT/US94/11390 (WO95/10514); PCT/US94/11391 (WO 95/10515); PCT/US94/11392 (WO95/10516); Stanley R. Sandler and Wolf Karo, Organic Functional Group Preparations, 2nd Edition, Academic Press, Inc., San Diego, Calif., Vol. 1–3, (1983), and in J. March, Advanced Organic Chemistry, Reactions & Mechanisms, and Structure, 3rd Edition, John Wiley & Sons, New York, 1346 pp. (1985). Alternative mechanistic pathways and analogous structures within the scope of the invention may be apparent to those skilled in the art.

ASSAYS

In vitro enzyme assays: FPT $IC_{50}$ (inhibition of farnesyl protein transferase, in vitro enzyme assay) are determined by the methods disclosed in WO/10515 or WO 95/10516. The data in the Examples demonstrate that the compounds of the invention are inhibitors of Ras-CVLS farnesylation by partially purified rat brain farnesyl protein transferase (FPT). The data also show that there are compounds of the invention which can be considered as potent ($IC_{50}$<<10 $\mu$M) inhibitors of Ras-CVLS farnesylation by partially purified rat brain FPT.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 70 percent active ingredient. Suitable solid carriers are known in the art, e.g. magnesium carbonate, magnesium stearate, talc, sugar, lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in unit dosage form. In such form, the preparation is subdivided into unit doses containing appropriate quantities of the active component, e.g., an effective amount to achieve the desired purpose.

The quantity of active compound in a unit dose of preparation may be varied or adjusted from about 0.1 mg to 1000 mg, more preferably from about 1 mg. to 300 mg, according to the particular application.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The amount and frequency of administration of the compounds of the invention and the pharmaceutically acceptable salts thereof will be regulated according to the judgment of the attending clinician considering such factors as age, condition and size of the patient as well as severity of the symptoms being treated. A typical recommended dosage regimen is oral administration of from 10 mg to 2000 mg/day preferably 10 to 1000 mg/day, in two to four divided doses to block tumor growth. The compounds are non-toxic when administered within this dosage range.

The following are examples of pharmaceutical dosage forms which contain a compound of the invention. The scope of the invention in its pharmaceutical composition aspect is not to be limited by the examples provided.

Pharmaceutical Dosage Form Examples

Example A—Tablets

| No. | Ingredients | mg/tablet | mg/tablet |
|---|---|---|---|
| 1. | Active compound | 100 | 500 |
| 2. | Lactose USP | 122 | 113 |
| 3. | Corn Starch, Food Grade, as a 10% paste in Purified Water | 30 | 40 |
| 4. | Corn Starch, Food Grade | 45 | 40 |
| 5. | Magnesium Stearate | 3 | 7 |
|  | Total | 300 | 700 |

Method of Manufacture

Mix Item Nos. 1 and 2 in a suitable mixer for 10–15 minutes. Granulate the mixture with Item No. 3. Mill the damp granules through a coarse screen (e.g., ¼", 0.63 cm) if necessary. Dry the damp granules. Screen the dried granules if necessary and mix with Item No. 4 and mix for 10–15 minutes. Add Item No. 5 and mix for 1–3 minutes. Compress the mixture to appropriate size and weigh on a suitable tablet machine.

Example B—Capsules

| No. | Ingredient | mg/capsule | mg/capsule |
|---|---|---|---|
| 1. | Active compound | 100 | 500 |
| 2. | Lactose USP | 106 | 123 |
| 3. | Corn Starch, Food Grade | 40 | 70 |
| 4. | Magnesium Stearate NF | 7 | 7 |
|  | Total | 253 | 700 |

Method of Manufacture

Mix Item Nos. 1, 2 and 3 in a suitable blender for 10–15 minutes. Add Item No. 4 and mix for 1–3 minutes. Fill the mixture into suitable two-piece hard gelatin capsules on a suitable encapsulating machine.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A compound which is:

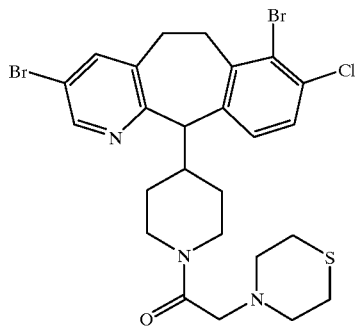

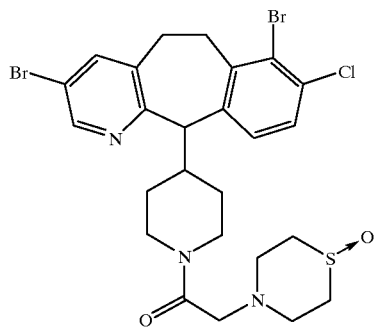

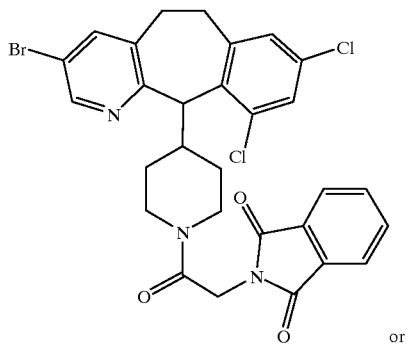

or

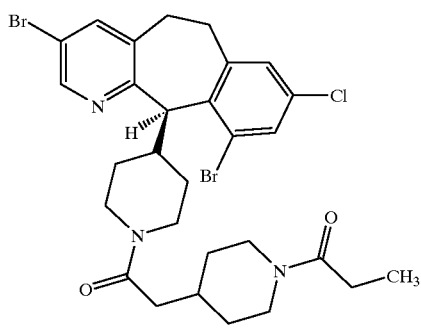

2. A pharmaceutical composition comprising an effective amount of the compound of claim 1 in combination with a pharmaceutically acceptable carrier.

3. A method for inhibiting the abnormal growth of tumor cells expressing an activated ras oncogene by the inhibition of ras farnesyl protein transferase in a human comprising administering to the human in need of such treatment an effective amount of a compound of claim 1.

4. The method of claim 3 wherein the cells inhibited are pancreatic tumor cells, lung cancer cells, myeloid leukemia tumor cells, thyroid follicular tumor cells, myelodysplastic tumor cells, epidermal carcinoma tumor cells, bladder carcinoma tumor cells or colon tumors cells.

5. The compound of claim 1 which is

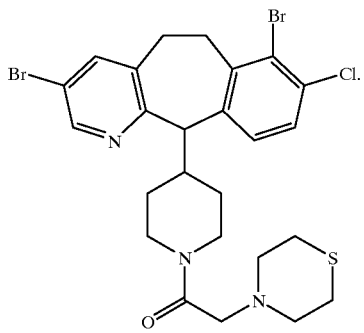

6. The compound of claim 1 which is

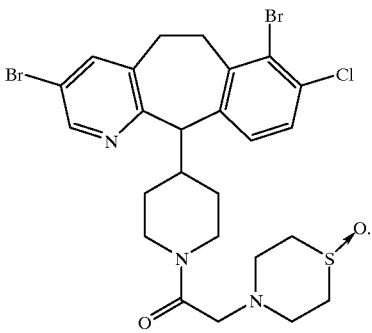

7. The compound of claim 1 which is

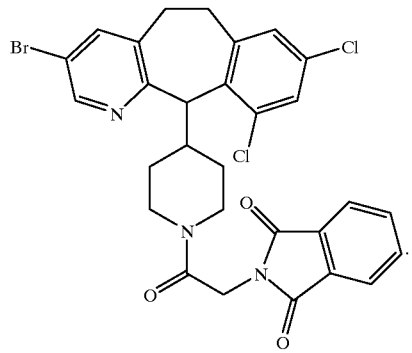

8. The compound of claim 1 which is

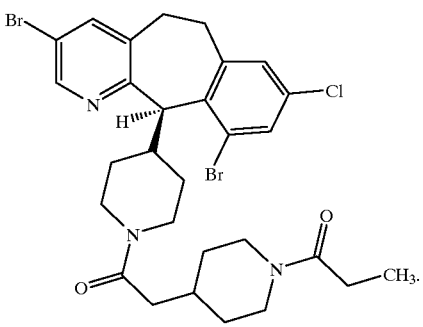

9. A pharmaceutical composition comprising an effective amount of the compound of claim 5 in combination with a pharmaceutically acceptable carrier.

10. A pharmaceutical composition comprising an effective amount of the compound of claim 6 in combination with a pharmaceutically acceptable carrier.

11. A pharmaceutical composition comprising an effective amount of the compound of claim 7 in combination with a pharmaceutically acceptable carrier.

12. A pharmaceutical composition comprising an effective amount of the compound of claim 8 in combination with a pharmaceutically acceptable carrier.

* * * * *